US00PP30037P2

(12) United States Plant Patent
O'Connell

(10) Patent No.: US PP30,037 P2
(45) Date of Patent: Dec. 25, 2018

(54) ***ECHEVERIA* PLANT NAMED 'PETRA'S PERLE'**

(50) Latin Name: *Echeveria hybrida*
Varietal Denomination: Petra's Perle

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,261

(22) Filed: Oct. 16, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Echeveria* cultivar named 'Petra's Perle' is disclosed, characterized by compact rosettes of foliage colored intense rose or violet-burgundy, depending upon environmental conditions. The new cultivar is robust growing, as compared to other commercially known *Echeverias*, enabling faster commercial production of the cultivar. The new cultivar 'Petra's Perle' can be propagated by leaves, enhancing commercial propagation. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

4 Drawing Sheets

Latin name of the genus and species: *Echeveria hybrida.*
Variety denomination: 'PETRA'S PERLE'.

BACKGROUND OF THE INVENTION

The new cultivar, *Echeveria* 'Petra's Perle', is the product of a planned breeding program. The new variety originated as a naturally occurring whole plant mutation of the unpatented parent, *Echeveria hybrida* 'Perle von Nurnberg'. The new cultivar 'Petra's Perle' was discovered by the inventor, Renee O' Connell, in June 2015, in Vista, Calif. at a commercial greenhouse.

Asexual reproduction of the new cultivar 'Petra's Perle' was first performed in Vista, Calif., at a commercial greenhouse, by terminal vegetative cuttings in August, 2015. *Echeveria* 'Petra's Perle' has since produced multiple generations and has shown that the unique features of this cultivar are stable and reproduced true to type.

SUMMARY OF THE INVENTION

The cultivar 'Petra's Perle' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PETRA'S PERLE'. These characteristics in combination distinguish 'PETRA'S PERLE' as a new and distinct *Echeveria* cultivar:

1 The rosettes of *Echeveria* 'Petra's Perle' are comprised of many leaves of nearly a taupe red rose in color, to violet-burgundy depending upon the light conditions.

2. *Echeveria* 'Petra's Perle' grows quickly, enhancing production times, as compared with many other *Echeverias.*
3. The new cultivar *Echeveria* 'Petra's Perle', a sport of *Echeveria* 'Perle von Nurnberg', displays a rosette color that is much more intense than the color displayed by a typical *Echeveria* 'Perle von Nurnberg'.
4. *Echeveria* 'Petra's Perle' can be propagated by leaves, thereby enhancing propagation in the commercial nursery.

PARENTAL COMPARISON

Plants of the new cultivar 'Petra's Perle' can be compared to plants of the unpatented, parent *Echeveria* 'Perle von Nurnberg', and are similar in most horticultural characteristics. However, plants of the new cultivar 'Petra's Perle' display a darker violet-burgundy foliage color, not displayed by *Echeveria* 'Perle von Nurnberg'. The new cultivar 'Petra's Perle' forms rosettes that are of more upright morphology than the rosettes of parent *Echeveria* 'Perle von Nurnberg'.

COMMERCIAL COMPARISON

The new cultivar 'Petra's Perle' can be compared to the unpatented commercial variety *Echeveria* 'Violet Queen'. Plants of the *Echeveria* 'Violet Queen' are similar to plants of the new cultivar 'Petra's Perle' in most horticultural characteristics. However, the new cultivar 'Petra's Perle' differs in the following:

1. *Echeveria* 'Petra's Perle' displays rosettes of a saturated rose to saturated rose to violet-burgundy color; as compared with the pallid milky color of *Echeveria* 'Violet Queen'.

2. *Echeveria* 'Petra's Perle' forms single rosettes that can grow to 5" in diameter, whereas *Echeveria* 'Violet Queen' produces smaller rosettes, and only attains a larger size by forming a cluster.
3. *Echeveria* 'Petra's Perle', due to its more saturated color, can be used in many more decorative projects as the rose burgundy provides aesthetic contrast with greens, blues, lilacs and other colors, whereas the pallid coloration of *Echeveria* 'Violet Queen' limits its use to subdued palettes in decorative projects.
4. *Echeveria* 'Petra's Perle' grows faster than *Echeveria* 'Violet Queen', thereby enhancing production times in a commercial nursery environment.
5. *Echeveria* 'Petra's Perle' has less disease pressure during the warmer summer months than does *Echeveria* 'Violet Queen'.

The new cultivar 'Petra's Perle' can be compared to the unpatented commercial variety *Graptoveria* 'Fred Ives'. Plants of the *Graptoveria* 'Fred Ives' are similar to plants of the new cultivar 'Petra's Perle' in most horticultural characteristics. However, the new cultivar 'Petra's Perle' differs in the following:

1. *Echeveria* 'Petra's Perle' forms rosettes of saturated rose to violet-leaves, as compared with the lilac leaves produced by *Graptoveria* 'Fred Ives'.
2. *Echeveria* 'Petra's Perle' exhibits a compact rosette morphology, whereas *Graptoveria* 'Fred Ives' grows with a taller shrub morphology.
3. *Echeveria* 'Petra's Perle', due to its saturated, unusual color and concentric rosettes, can be more readily utilized for decorative uses such as bouquets, entertainment centerpieces and to provide accent colors for other colors, such as greens, blues, whites, and others, than can *Graptoveria* 'Fred Ives' with its monotone lilac branches.
4. *Echeveria* 'Petra's Perle', due to its saturated leaf color, contrasted by light colored hyaline margins, produces a more attractive rosette than does *Graptoveria* 'Fred Ives', with its monotone lilac rosette, and no discernible contrasting margin.

BRIEF DESCRIPTION OF THE PHOTOGRAPHS

The accompanying photographs in FIG. 1 through FIG. 4 illustrate in full color typical plants of 'PETRA'S PERLE' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

Figure 1:
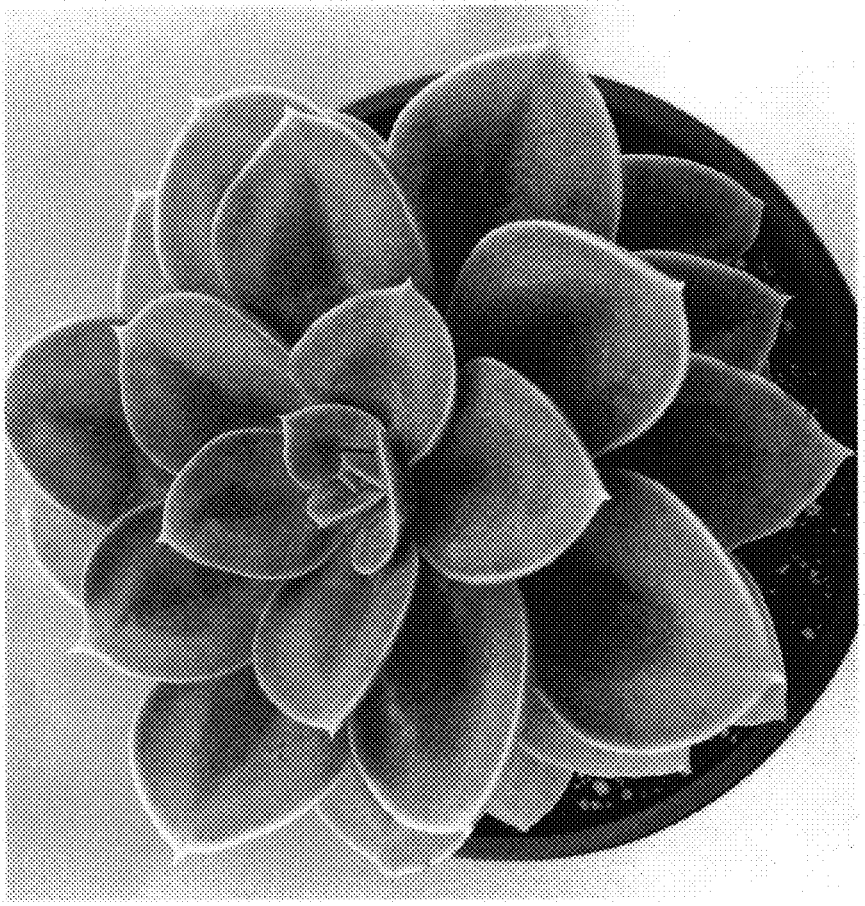
FIG. 1 illustrates in full color a plant of *Echeveria* 'Petra's Perle', grown in a greenhouse (approximately 2000 foot candles) in Vista, Calif. during the Spring and Summer months.
Figure 2:
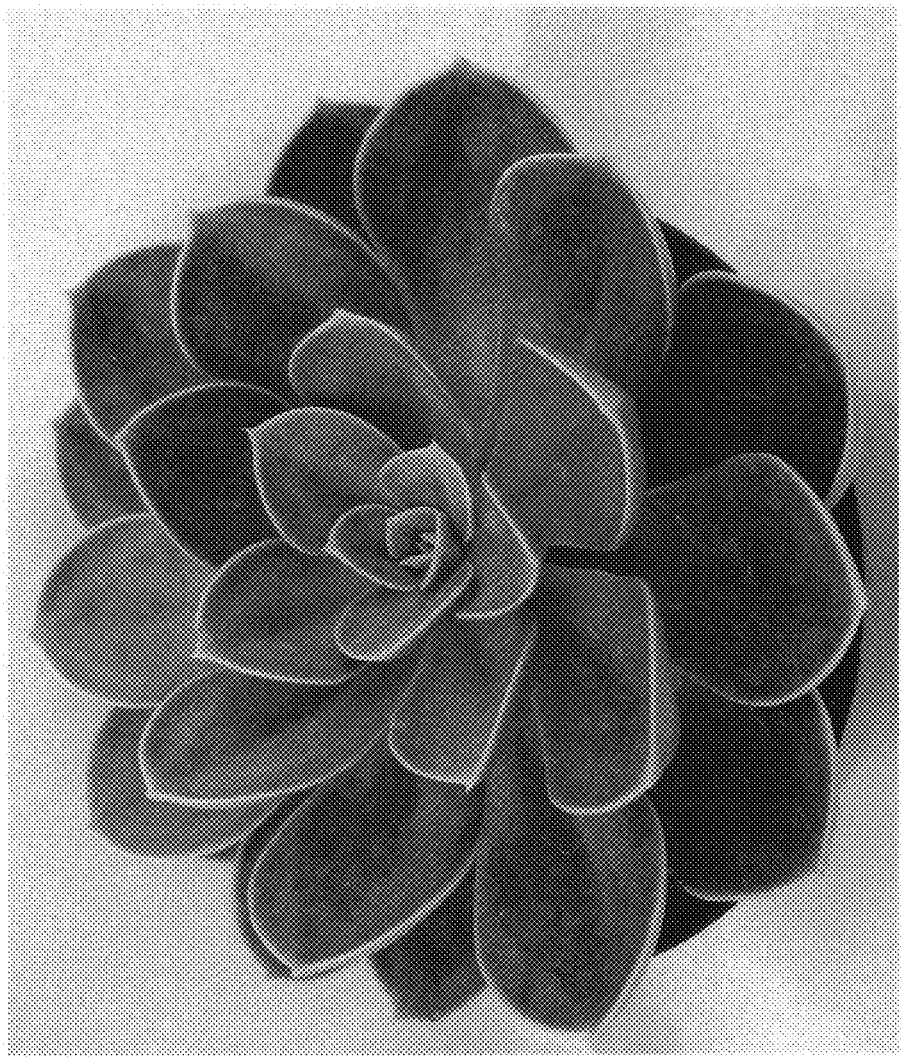
FIG. 2 illustrates in full color the rosette of different plant of *Echeveria* 'Petra's Perle' during winter months, grown in a greenhouse (approximately 2000 foot candles) in Vista, Calif.
Figure 3:
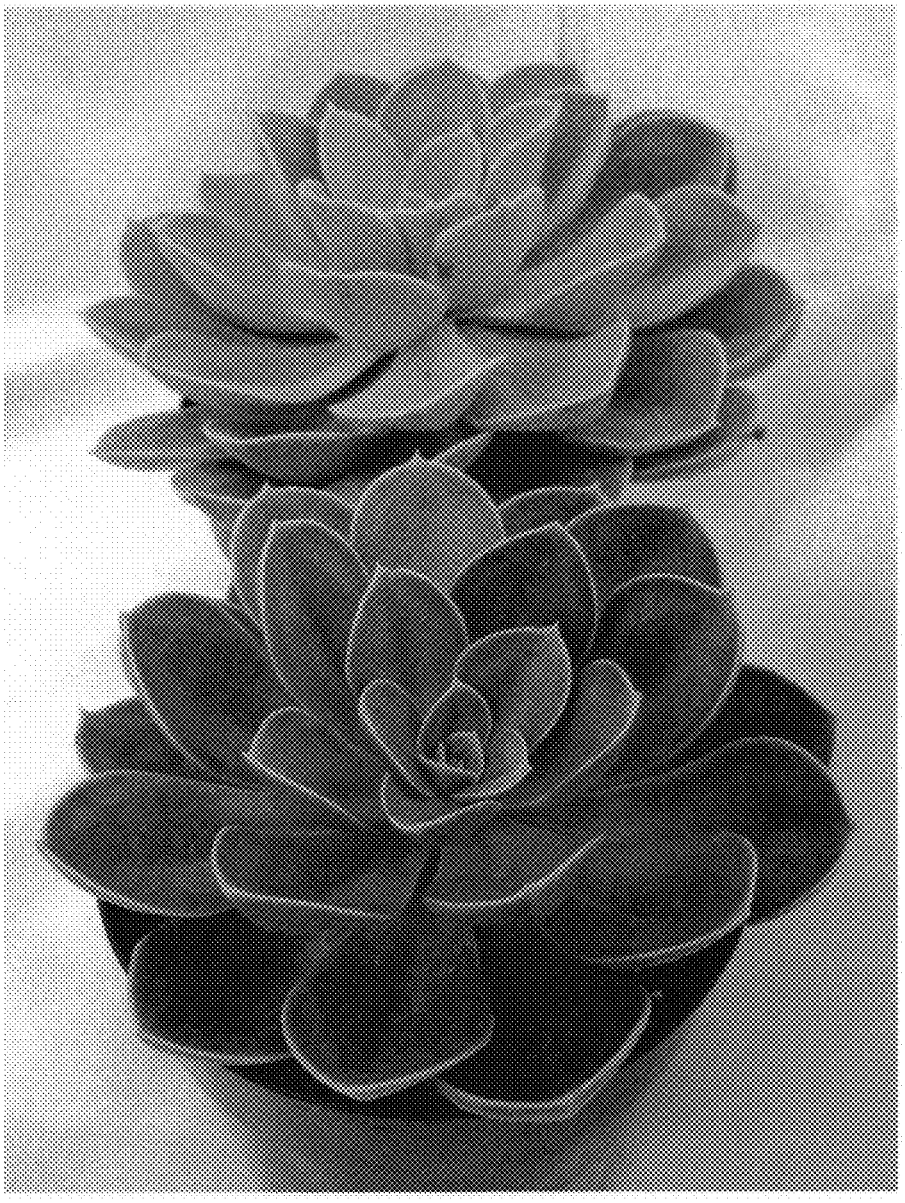

FIG. 3 illustrates in full color the comparison in color between *Echeveria* 'Petra's Perle' and *Echeveria* 'Perle von Nurnberg'. Plants of 'Petra's Perle' are pictured towards the front, plants of 'Perle von Nurnberg' are in the back. Plants are approximately the same age.

Figure 4:
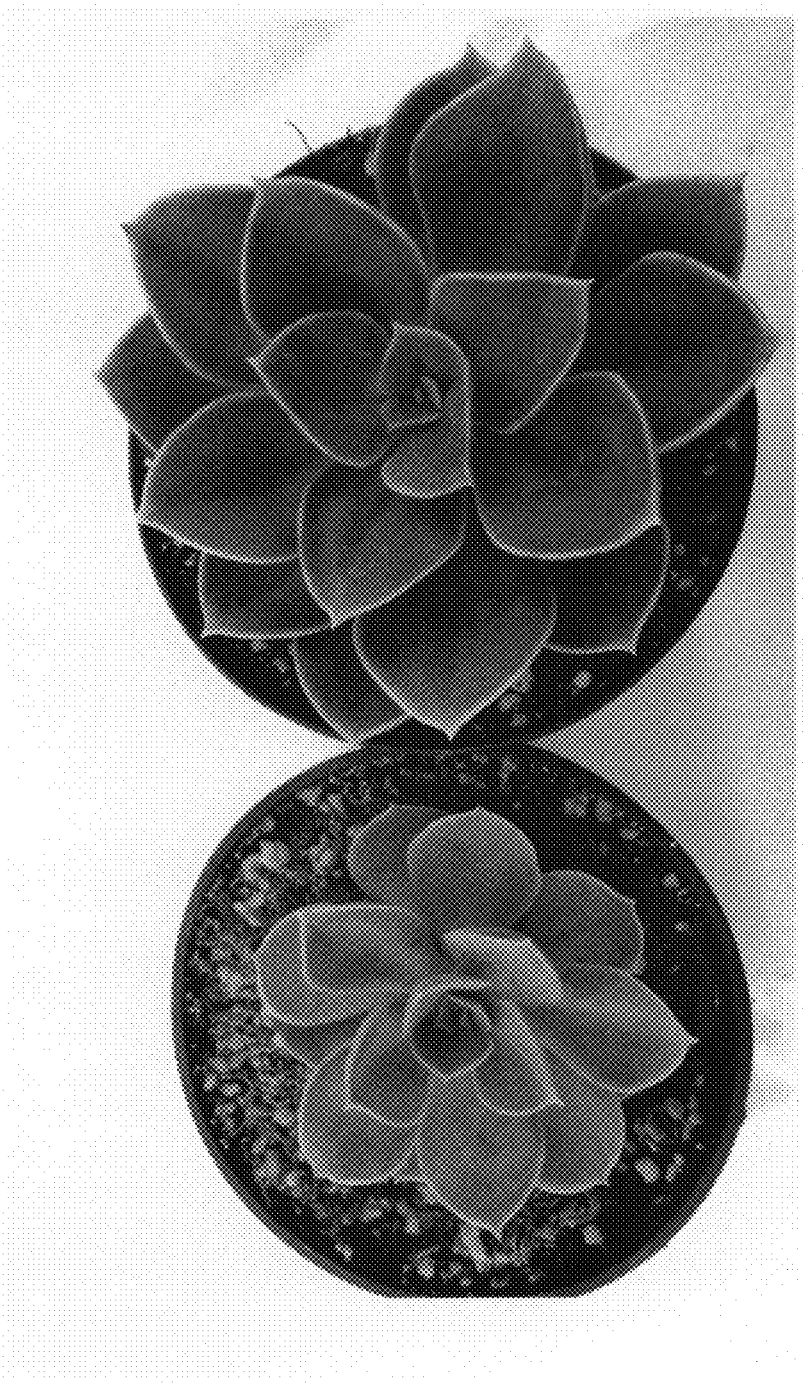

FIG. 4 illustrates in full color the comparison in color between a cutting of *Echeveria* 'Petra's Perle' and a cutting of *Echeveria* 'Magic Red' (not patented acquired from Greenex Worldwide Export). Plants of 'Petra's Perle' are pictured on the right, plants of 'Magic Red' are on the left.

DETAILED BOTANICAL DESCRIPTION

In the following description, color references are made to The Royal Horticultural Society Colour 2007 Chart, except where general terms of ordinary dictionary significance are used. The following observations and measurements describe 'Petra's Perle' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'PETRA'S PERLE'.

PROPAGATION

Type of propagation typically used: Terminal vegetative cuttings.

Time to initiate roots: About 11 days at approximately 24° C.

Root description: Fibrous.

PLANT

Age of plant described: Approximately 6 months from a cutting.

Container size of the plant described: 1 gallon.

Growth habit: Upright rosulate plant.

Height: Approximately 10 to 14 cm.

Plant spread: Approximately 15 to 18 cm.

Growth rate: Rapid.

Branching characteristics: Not typically observed.

FOLIAGE

Leaf:

*Arrangement*.—Rosulate.

*Average length*.—6 cm.

*Average width*.—3.2 to 4.0 cm.

*Width at base*.—Average 1.7 cm.

*Aspect of leaf*.—Leaf slightly cupped upward.

*Leaf thickness*.—About 1.0 cm at thickest point at center of leaf.

*Shape of blade*.—Short spatulate.

*Apex*.—Broad mucronate. Mucronate tip 2 to 3 mm long, moderately sharp.

*Base*.—Broad attenuate.

*Margin*.—Entire.

*Texture of top surface*.—Glabrous. Very slightly glaucous.

*Texture of bottom surface*.—Glabrous. Very slightly glaucous.

*Appearance of top surface*.—Matte.

*Appearance of bottom surface*.—Matte.

*Quantity of leaves per plant*.—Average range 25 to 35.

*Color*.—Young foliage upper side: Near RHS Greyed-Red 182A Apical margin coloration near Yellow-Green 151D. Lower margin Red 50A. Young foliage under side: Near RHS Greyed-Red 181B. Apical margin coloration near Yellow-Green 151D. Lower margin Red 50A. Mature foliage upper side: Near RHS Yellow-Green 153D heavily flushed Greyed-Red 181B. Margin Yellow-Green 150D. Lower margin flushed Red 46C. Mature foliage, under side: Near RHS Yellow-Green 153D heavily flushed Greyed-Red 181B. Margin Yellow-Green 150D.

*Winter color*.—Young foliage upper side: Base color near RHS Yellow-Green 153C covered Greyed-Orange 173A. Apical margin coloration near Yellow-Green 150D. Lower section of leaf flushed Greyed-Red 179A inside Yellow-Green margin. Young foliage under side: Base color near RHS Yellow-Green 153C covered Greyed-Orange 173A. Apical margin coloration near Yellow-Green 150D. Mature foliage upper side: Near RHS Yellow-Green 153D flushed Greyed-Orange 172C towards base. Margin Yellow-Green 151D. Mature foliage, under side: Near RHS Yellow-Green 153D flushed Greyed-Orange 172C towards base. Margin. Yellow-Green 151D.

FLOWER

Flowering not observed.

REPRODUCTIVE ORGANS

Not observed.

OTHER CHARACTERISTICS

Temperature tolerance: Tolerates temperatures from approximately −2° C. to at least 35° C.

Disease/pest resistance: Less disease pressure during Summer observed. Neither resistance or susceptibility to pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'PETRA'S PERLE' as herein illustrated and described.

* * * * *